US00PP32289P2

(12) United States Plant Patent
Hansen

(10) Patent No.: US PP32,289 P2
(45) Date of Patent: Oct. 6, 2020

(54) **X *MANGAVE* PLANT NAMED 'FROSTED ELEGANCE'**

(50) Latin Name: ***Agave times* x *Mangave* hybrid**
Varietal Denomination: Frosted Elegance

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,324

(22) Filed: Sep. 13, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
CPC ... A01H 5/12; A01H 5/02; A01H 5/00; A01H 6/12; A01H 1/02
See application file for complete search history.

(56) References Cited

U.S. PATENT DOCUMENTS

PP31,251 P2 * 12/2019 Hansen ..... A01H 5/12 Plt./373
PP31,274 P2 * 12/2019 Hansen ..... A01H 5/12 Plt./373
PP31,601 P2 * 3/2020 Hansen ..... A01H 6/12 Plt./373
PP31,630 P2 * 3/2020 Hansen ..... A01H 6/12 Plt./373

OTHER PUBLICATIONS

Bock's blog. Succulents and More New Hans Hansen x*Mangave* releases for 2019, retrieved on Apr. 6, 2020, retrieved from the internet at https://www.succulentsandmore.com/2019/02/new-hans-hansen-mangave-releases-for.html, 11 pp. (Year: 2019).*

* cited by examiner

*Primary Examiner* — June Hwu

(57) ABSTRACT

A new and unique x *Mangave* plant named 'Frosted Elegance' characterized by moderate to slow growth rate, compact habit and lanceolate foliage with glaucous blue-green margins and light blue-chartreuse centers with sharp firm mucro and flexible marginal teeth that become firm as they develop more pigment distally to greyed-purple.

1 Drawing Sheet

Botanical classification: *Agave* times x *Mangave* hybrid.
Variety denomination: 'Frosted Elegance'.

STATEMENT REGARDING PRIOR DISCLOSURES UNDER 37 CFR 1.77(B)(6)

The first non-enabling disclosure of the claimed plant, in the form of a private sale, was made by Walters Gardens, Inc. on Oct. 15, 2018 to Plant Delights Nursery, Inc. Plants for this sale were obtained from the inventor. Since then, on Oct. 22, 2019 the plant was sold to Wild Thing Nursery, on Dec. 17, 2018 was sold to Hine Growers, Inc. and on Jan. 14, 2019 to In The Country Gardens & Gifts by Walters Gardens, Inc. Walters Gardens, Inc. received the new plant and all information on the plants from the inventor. No plants of x *Mangave* 'Frosted Elegance' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* plant, x *Mangave* 'Frosted Elegance' that was hybridized by the inventor at a wholesale perennial nursery in Zeeland, Mich., USA as a cross between a proprietary unnamed selection of *Agave nizandensis* (not patented) as the female or seed parent times and x *Mangave* 'Bloodspot' (not patented) as the male or pollen parent. The cross was performed Jul. 10, 2014 and seeds were harvested and sown later the following autumn. Through trials at the same nursery the plant was referred to by the code 14-171-12. The new plant has been successfully asexually propagated by sterile shoot-tip tissue culture and by basal offsets at the same nursery in Zeeland, Mich. The asexual propagation by tissue culture and basal offsets has been found to produce stable and identical plants that maintain all the unique characteristics of the original plant.

BRIEF SUMMARY OF THE INVENTION

X *Mangave* 'Frosted Elegance' differs from its parents as well as all other *Manfreda, Agave* and x *Mangave* known to the applicant. The female parent has a flatter habit with fewer leaves per plant, with narrow, dark-green, longer, arching foliage that has small marginal teeth, moderately channeled or concavo-convex with a lighter chartreuse in the center along midrib. The new plant has glaucous blue-green margins and light blue-chartreuse center. The male parent is more upright in habit with greater number of leaves per plant, with foliage that is shorter, more glaucous, thicker (adaxial to abaxial), dark brown around the marginal teeth and larger terminal spines, mahogany spotting and lacks the lighter center band.

The most similar known X *Mangave* cultivars known to the inventor are: 'Blue Dart' (not patented), 'Blazing Saddles' U.S. Plant Pat. No. 31,274, 'Desert Dawn' copending U.S. Plant patent application Ser. No. 16/602,323, 'Racing Stripes' U.S. Plant Pat. No. 31,251, 'Shadow Waltz' U.S. Plant Pat. No. 31,601 and 'Painted Desert' U.S. Plant Pat. No. 31,630.

'Blue Dart' is a larger plant with broader foliage, the foliage is thicker, and has a brown margin, marginal teeth and apical spine and lacks the lighter blue-green center band. 'Blazing Saddles' has a larger habit with foliage that is broader, more lustrous, less glaucous leaves with reddish spotting in high light intensity. 'Desert Dawn' has a larger habit, broader foliage, smaller marginal teeth, less glaucous and the foliage is more solid greyed-purple with a purple center stripe in high ultraviolet light. 'Racing Stripes' has larger habit, leaves that are shiny deep green on the margins and chartreuse-yellow in the center midrib and the larger teeth and apical spine are yellowish as the leaf is expanding and develop a cinnamon color when mature. 'Shadow Waltz' has narrow arching leaves with broad dark green margin and light green to chartreuse center. 'Painted Desert' has a larger more horizontal habit, foliage with more flexible marginal teeth and lacks the semi-flexible mucro at the leaf apex and also the greyed-purple spotting on the leaf surfaces.

The new plant, 'Frosted Elegance', is unique from all of these variegated *Agave*, x *Mangave* and *Manfreda* known to the inventor by the following combined traits:

1. Compact habit with about 46 leaves;
2. Foliage lanceolate with small semi-flexible marginal teeth becoming firm with maturity and firm sharp apical mucro;
3. Foliage has glaucous blue-green margins and light blue-chartreuse center above, solid blue-green below;
4. Moderate growth rate;

BRIEF DESCRIPTION OF THE DRAWINGS

The photograph of the new plant demonstrates the overall appearance of the new plant including the unique traits as a three-year-old plant grown in a container initially in a greenhouse and followed up with growing in an outdoor trial garden with supplemental water and fertilizer as needed. The colors are as accurate as reasonably possible with color reproductions. Ambient light spectrum, temperature, source and direction may cause the appearance of minor variation in color.

FIG. 1 shows the new plant in the landscape.

FIG. 2 shows a close-up of the foliage of the new plant.

DETAILED BOTANICAL DESCRIPTION

The following descriptions and color references are based on the 2015 edition of The Royal Horticultural Society Colour Chart except where common dictionary terms are used. The new plant, x *Mangave* 'Frosted Elegance', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Botanical classification: *Agave* times x *Mangave* hybrid;

Variety denomination: 'Frosted Elegance';

Parentage: A proprietary unnamed selected form of *Agave nizandensis* as the female or seed parent; x *Mangave* 'Bloodspot' as the male or pollen parent;

Propagation: Removal offsets, core division and sterile plant tissue culture;

Time to initiate roots from tissue culture: About 21 days;

Growth rate: Moderate;

Crop time: About 18 to 20 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 46 fleshy leaves radially emerging and outwardly reaching from central rhizome, producing a symmetrical rounded mound;

Plant size: Foliage height about 17.0 cm tall from soil line to the top of the leaves and to about 38.0 cm wide at the widest point at soil line;

Foliage description: Lanceolate; simple; sarcous; fibrous; glabrous; margins finely dentate with semi-flexible teeth; apex acute with firm mucro; base truncate, sessile, semi-clasping;

Leaf size: To about 18.0 cm long, about 35.0 mm wide near middle and 5.0 mm thick near base, average about 15.5 cm long, 30.0 mm wide and 5.0 mm thick; typically bi-laterally symmetrical; glabrous and glaucous above and below; margin to about 14.0 mm wide and center to about 12.0 mm wide; teeth initially flexible becoming firm, curved backward slightly toward stem; 2.0 mm long and 3.0 mm across at base about 8.0 mm apart; mucro about 5.0 mm long and 1.0 mm wide;

Foliage fragrance: None observed;

Leaf blade color:

*Adaxial* (*low ultraviolet exposure*).—Young and mature margin between RHS 146B and RHS N138C, center nearest RHS N148C.

*Abaxial* (*low ultraviolet exposure*).—Young and mature margin and center between RHS 146B and RHS N138C.

*Adaxial* (*high ultraviolet exposure*).—Young and mature margin between RHS 146B and RHS N138C, center nearest RHS N148C.

*Abaxial* (*high ultraviolet exposure*).—Young margin and center nearest blend between RHS 148B, RHS N138C and RHS 191B.

*Teeth*.—Abaxial and adaxial on young foliage nearest RHS 160C; on mature foliage distally nearest RHS 187C and proximally nearest RHS 191D.

Mucro: Terminal spine; firm; straight; sharply pointed; about 5.0 mm long and 1.0 mm wide;

*Mucro color*.—Abaxial and adaxial on young foliage between RHS 187A and RHS 187B; on mature foliage nearest RHS N187A.

Petiole: Sessile;

Veins: Parallel; not distinct;

Flowering a fruiting has not yet been observed.

Disease resistance: x *Mangave* 'Frosted Elegance' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Mangave* plant named 'Frosted Elegance' as herein described and illustrated.

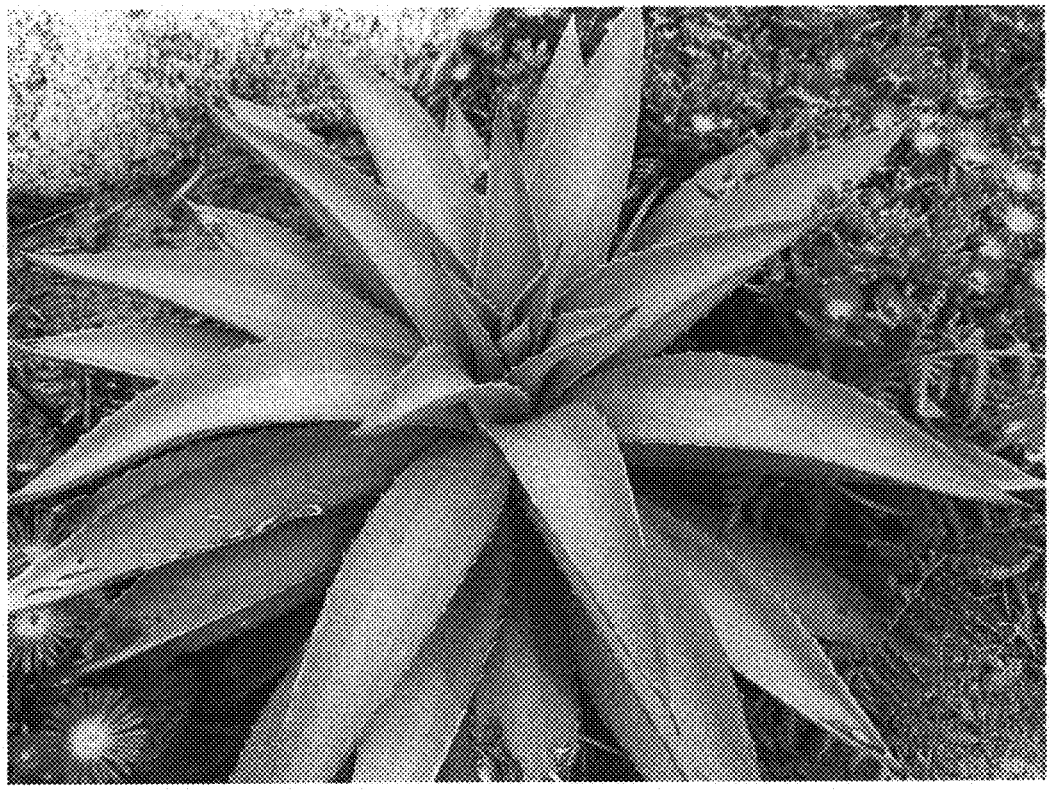
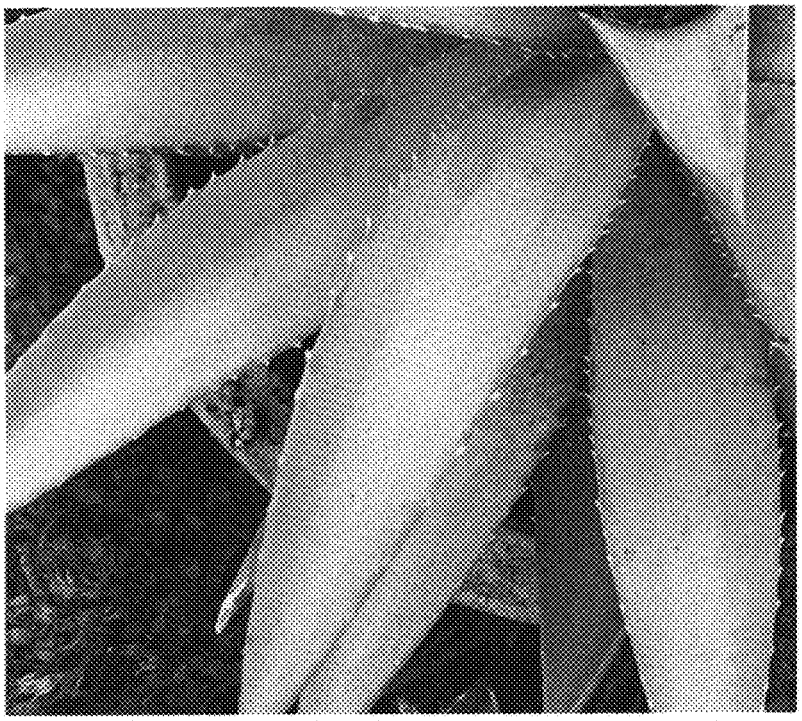

* * * * *